(12) United States Patent
Kaye

(10) Patent No.: US 9,211,372 B2
(45) Date of Patent: Dec. 15, 2015

(54) SYSTEMS AND METHODS FOR LIMB TREATMENT

(75) Inventor: David Martin Kaye, Beaumaris (AU)

(73) Assignee: Osprey Medical, Inc., Minnetonka, MN (US)

( * ) Notice: Subject to any disclaimer, the term of this patent is extended or adjusted under 35 U.S.C. 154(b) by 0 days.

(21) Appl. No.: 13/571,823

(22) Filed: Aug. 10, 2012

(65) Prior Publication Data

US 2013/0079697 A1   Mar. 28, 2013

Related U.S. Application Data

(60) Provisional application No. 61/523,042, filed on Aug. 12, 2011, provisional application No. 61/522,605, filed on Aug. 11, 2011.

(51) Int. Cl.
*A61M 1/36* (2006.01)
*A61M 1/16* (2006.01)
*A61M 5/142* (2006.01)
*A61M 25/10* (2013.01)

(52) U.S. Cl.
CPC ............ *A61M 1/3659* (2014.02); *A61M 1/1698* (2013.01); *A61M 1/3621* (2013.01); *A61M 5/142* (2013.01); *A61M 25/10* (2013.01); *A61M 2025/1095* (2013.01); *A61M 2202/0021* (2013.01); *A61M 2210/086* (2013.01); *A61M 2210/12* (2013.01)

(58) Field of Classification Search
CPC .................. A61M 2025/1097; A61M 1/3621; A61M 2210/08
See application file for complete search history.

(56) References Cited

U.S. PATENT DOCUMENTS

| | | | |
|---|---|---|---|
| 3,931,815 A | 1/1976 | Takatsuki |
| 4,054,137 A | 10/1977 | Lee et al. |
| 4,581,017 A | 4/1986 | Sahota |
| 4,592,341 A | 6/1986 | Omagari et al. |
| 4,795,427 A | 1/1989 | Helzel |
| 4,838,872 A | 6/1989 | Sherlock |

(Continued)

FOREIGN PATENT DOCUMENTS

| | | |
|---|---|---|
| DE | 10102045 | 1/2003 |
| EP | 0301854 | 2/1989 |

(Continued)

OTHER PUBLICATIONS (Fried SJ, Miller R, Weaver, FA, Faddis, D. Safe, compact and portable system for regional chemotherapeutic hyperthermic perfusion procedures. J Extracorporeal Tech. 25:1 22-26 (1993).*

(Continued)

*Primary Examiner* — Leslie Deak

(57) ABSTRACT

A method of delivering a medicament to a limb of a patient body includes isolating a circulatory system of the limb from a circulatory system of the patient body, wherein the limb circulatory system is substantially all limb arteries and substantially all limb veins located between an isolation region and an end of the limb. A perfusion catheter is inserted into a limb artery in an antegrade position, while a collection catheter is inserted into a limb vein in a retrograde position. The blood flow of the limb circulatory system is then circulated by collecting the blood flow with the collection catheter and delivering the blood flow with the perfusion catheter. A medicament is perfused into the limb circulatory system with the perfusion catheter.

10 Claims, 12 Drawing Sheets

(56) References Cited

U.S. PATENT DOCUMENTS

| | | |
|---|---|---|
| 4,969,470 A | 11/1990 | Mohl et al. |
| 5,069,662 A * | 12/1991 | Bodden .................. 604/5.01 |
| 5,338,662 A | 8/1994 | Sadri |
| 5,423,745 A | 6/1995 | Todd et al. |
| 5,494,822 A | 2/1996 | Sadri |
| 5,807,311 A | 9/1998 | Palestrant |
| 5,807,318 A | 9/1998 | St. Goar et al. |
| 5,807,322 A | 9/1998 | Lindsey et al. |
| 5,810,757 A | 9/1998 | Sweezer, Jr. et al. |
| 5,813,842 A | 9/1998 | Tamari |
| 5,843,016 A | 12/1998 | Lugnani et al. |
| 5,871,464 A | 2/1999 | Tryggvason et al. |
| 5,871,465 A | 2/1999 | Vasko |
| 6,021,340 A | 2/2000 | Randolph et al. |
| 6,080,170 A | 6/2000 | Nash et al. |
| 6,093,392 A | 7/2000 | High et al. |
| 6,110,139 A | 8/2000 | Loubser |
| 6,152,141 A | 11/2000 | Stevens et al. |
| 6,186,146 B1 | 2/2001 | Glickman |
| 6,251,093 B1 | 6/2001 | Valley et al. |
| 6,254,563 B1 | 7/2001 | Macoviak et al. |
| 6,295,990 B1 | 10/2001 | Lewis et al. |
| 6,342,214 B1 | 1/2002 | Tryggvason et al. |
| 6,376,471 B1 | 4/2002 | Lawrence, III et al. |
| 6,398,752 B1 | 6/2002 | Sweezer et al. |
| 6,481,439 B1 | 11/2002 | Lewis et al. |
| 6,500,158 B1 | 12/2002 | Ikeguchi |
| 6,508,777 B1 | 1/2003 | Macoviak et al. |
| 6,554,819 B2 | 4/2003 | Reich |
| 6,558,349 B1 | 5/2003 | Kirkman |
| 6,569,147 B1 | 5/2003 | Evans et al. |
| 6,585,716 B2 | 7/2003 | Altman |
| 6,595,963 B1 | 7/2003 | Barbut |
| 6,638,264 B1 | 10/2003 | Tryggvason et al. |
| 6,638,268 B2 | 10/2003 | Niazi |
| 6,673,039 B1 | 1/2004 | Bridges et al. |
| 6,689,090 B1 | 2/2004 | Tryggvason et al. |
| 6,699,231 B1 * | 3/2004 | Sterman et al. ............. 604/509 |
| 6,726,651 B1 | 4/2004 | Robinson et al. |
| 6,935,344 B1 | 8/2005 | Aboul-Hosn et al. |
| 6,980,843 B2 | 12/2005 | Eng et al. |
| 6,992,070 B2 | 1/2006 | Donahue et al. |
| 7,211,073 B2 | 5/2007 | Fitzgerald et al. |
| 7,300,429 B2 | 11/2007 | Fitzgerald et al. |
| 7,331,922 B2 | 2/2008 | Mohl |
| 7,363,072 B2 | 4/2008 | Movahed |
| 7,722,596 B2 | 5/2010 | Shapland et al. |
| 8,152,786 B2 * | 4/2012 | Shapland et al. ............. 604/321 |
| 8,292,871 B2 | 10/2012 | Shapland et al. |
| 2001/0052345 A1 | 12/2001 | Niazi |
| 2002/0062121 A1 | 5/2002 | Tryggvason et al. |
| 2002/0077595 A1 | 6/2002 | Hundertmark et al. |
| 2002/0091349 A1 | 7/2002 | Reich |
| 2002/0099254 A1 | 7/2002 | Movahed |
| 2002/0107504 A1 | 8/2002 | Gordon |
| 2002/0165598 A1 | 11/2002 | Wahr et al. |
| 2002/0169436 A1 | 11/2002 | Gurm et al. |
| 2003/0138350 A1 | 7/2003 | Macoviak |
| 2003/0163081 A1 | 8/2003 | Constantz et al. |
| 2003/0191434 A1 | 10/2003 | Dorros et al. |
| 2003/0199917 A1 | 10/2003 | Knudson et al. |
| 2003/0236533 A1 | 12/2003 | Wilson et al. |
| 2004/0002159 A1 | 1/2004 | Xiao et al. |
| 2004/0030286 A1 | 2/2004 | Altman |
| 2004/0099596 A1 | 5/2004 | Naghavi et al. |
| 2004/0102732 A1 | 5/2004 | Naghavi et al. |
| 2004/0102766 A1 | 5/2004 | Poleo, Jr. |
| 2004/0210239 A1 | 10/2004 | Nash et al |
| 2004/0254523 A1 | 12/2004 | Fitzgerald et al. |
| 2005/0010189 A1 | 1/2005 | Toomey et al. |
| 2005/0124969 A1 | 6/2005 | Fitzgerald et al. |
| 2005/0137539 A1 | 6/2005 | Biggie et al. |
| 2005/0192548 A1 | 9/2005 | Dolliver et al. |
| 2005/0197531 A1 | 9/2005 | Cabiri et al. |
| 2005/0226855 A1 | 10/2005 | Alt et al. |
| 2005/0256441 A1 | 11/2005 | Lotan et al. |
| 2005/0273014 A1 | 12/2005 | Gianchandi et al. |
| 2006/0013772 A1 | 1/2006 | LeWinter et al. |
| 2007/0038170 A1 | 2/2007 | Joseph et al. |
| 2007/0078352 A1 | 4/2007 | Pijls |
| 2007/0118072 A1 | 5/2007 | Nash |
| 2007/0135779 A1 | 6/2007 | Lalomia et al. |
| 2007/0203445 A1 | 8/2007 | Kaye et al. |
| 2007/0255162 A1 | 11/2007 | Abboud et al. |
| 2008/0021314 A1 | 1/2008 | Movahed |
| 2008/0108960 A1 | 5/2008 | Shapland et al. |
| 2008/0125698 A1 | 5/2008 | Gerg et al. |
| 2008/0125746 A1 | 5/2008 | Shapland et al. |
| 2008/0306425 A1 | 12/2008 | Al-Rashdan |
| 2009/0018526 A1 | 1/2009 | Power et al. |
| 2009/0069829 A1 | 3/2009 | Shturman |
| 2009/0187131 A1 | 7/2009 | Fitzgerald et al. |
| 2009/0234321 A1 | 9/2009 | Shapland et al. |
| 2009/0312696 A1 | 12/2009 | Copa et al. |
| 2010/0041984 A1 | 2/2010 | Shapland et al. |
| 2010/0042069 A1 | 2/2010 | Shapland et al. |
| 2010/0082004 A1 | 4/2010 | Shapland et al. |
| 2010/0168564 A1 | 7/2010 | Shapland et al. |
| 2010/0274173 A1 | 10/2010 | Shapland et al. |
| 2011/0015558 A1 | 1/2011 | Kaye et al. |
| 2011/0172558 A1 | 7/2011 | Shapland et al. |
| 2014/0188062 A1 | 7/2014 | James et al. |
| 2015/0182684 A1 | 7/2015 | Kaye et al. |
| 2015/0190564 A1 | 7/2015 | Kaye |

FOREIGN PATENT DOCUMENTS

| | | |
|---|---|---|
| EP | 0150960 | 1/1990 |
| EP | 0526102 | 4/1998 |
| EP | 1859826 | 11/2007 |
| GB | 2125487 | 3/1984 |
| JP | 2001-526071 | 12/2001 |
| WO | WO 89/01309 | 2/1989 |
| WO | WO 92/20387 | 11/1992 |
| WO | WO 98/31405 | 7/1998 |
| WO | WO 98/56440 | 12/1998 |
| WO | WO 99/29227 | 6/1999 |
| WO | WO 99/30765 | 6/1999 |
| WO | WO 99/31982 | 7/1999 |
| WO | WO 99/60097 | 12/1999 |
| WO | WO 01/00268 | 1/2001 |
| WO | WO 01/13983 | 3/2001 |
| WO | WO 01/83004 | 11/2001 |
| WO | WO 01/97901 | 12/2001 |
| WO | WO 02/60511 | 8/2002 |
| WO | WO 02/087677 | 11/2002 |
| WO | WO 03/070330 | 8/2003 |
| WO | WO 2004/083817 | 9/2004 |
| WO | WO 2005/027995 | 3/2005 |
| WO | WO 2005/082440 | 9/2005 |
| WO | WO 2006/004882 | 1/2006 |
| WO | WO 2006/042219 | 4/2006 |
| WO | WO 2007/002154 | 1/2007 |
| WO | WO 2007/143288 | 12/2007 |
| WO | WO 2008/122048 | 10/2008 |

OTHER PUBLICATIONS

Alfayoumi, F. et al., "The No-Reflow Phenomenon: Epidemiology, Pathophysiology, and Therapeutic Approach," Reviews in Cardiovascular Medicine, vol. 6, No. 2, pp. 72-83 (2005).

Assali, A. et al., "Intracoronary Adenosine Administered During Percutaneous Intervention in Acute Myocardial Infarction and Reduction in the Incidence of "No Reflow" Phenomenon," Catheterization and Cardiovascular Interventions, vol. 51, pp. 27-31 (2000).

de Lemos, J. et al., "New tools for assessing microvascular obstruction in patients with ST elevation myocardial infarction," Heart, vol. 90, pp. 119-120 (2004).

del Monte et al., "Improvement in Survival and Cardiac Metabolism After Gene Transfer of Sarcoplasmic Reticulum CA2+-ATPase in a Rat Model of Heart Failure", Circulation, 104(12): 1424-1429, 2001.

(56) References Cited

OTHER PUBLICATIONS

Hajjar et al., "Modulation of Ventricular Function Through Gene Transfer in Vivo", Proc. Natl. Acad. Sci., USA, 95: 5251-5256, 1998.

Kramer, c., "The prognostic significance of microvascular obstruction after myocardial infarction as defined by cardiovascular magnetic resonance," European Heart Journal, vol. 26, pp. 532-533 (2005).

Logeart, D. et al., "How to Optimize in Vivo Gene Transfer to Cardiac Myocytes: Mechanical or Pharmacological Procedures?", Human Gene Therapy, 12: 1601-1610, 2001.

Marzilli, M. et al., "Primary coronary angioplasty in acute myocardial infarction: Clinical correlates of the 'no reflow' phenomonen," International Journal o/Cardiology, vol. 65 (Suppl. I), pp. S23-S28 (1998).

Michishita, et al. "A Novel Contrast Removal System From The Coronary Sinus Using an Absorbing Column During Coronary Angiography in a Porcine Model", Journal of the American College of Cardiology, vol. 47, No. 9 (2006).

Resnic, F. et al., "No-reflow is an independent predictor of death and myocardial infarction after percutaneous coronary intervention," American Heart Journal, vol. 145, No. I, pp. 42-46.

Schrader, "Contrast Media-Induced Renal Failure: And Overview", Journal of Interventional Cardiology, vol. 18, No. 6, pp. 417-423 (2005).

Vogel, Robert et al., Transcatheter Coronary Artery Diagnostic Techniques, Texas Heart Institute Journal, vol. 16, No. 3, dated 1989; 9 pgs.

PCT International Search Report and Written Opinion in International Application PCT/US2012/050277, mailed Mar. 4, 2013, 9 pgs.

\* cited by examiner

| TIME | 0 | | 15 MIN | | 30 MIN | | 40 MIN | | 24 HOUR | | DAY 5 | | UNITS | REFERENCE RANGE |
|---|---|---|---|---|---|---|---|---|---|---|---|---|---|---|
| | AVE | SEM | AVE | SEM | AVE | SEM | AVE | SEM | AVE | SEM | AVE | SEM | | |
| HEMATOLOGY | | | | | | | | | | | | | | |
| RED CELL COUNT | 7.3 | 0.3 | 5.5 | 0.5 | 5.2 | 0.6 | 6.9 | 0.3 | 9.3 | 0.5 | 7.7 | 0.3 | $\times 10^{12}$/L | 9.00 - 15.00 |
| HAEMOGLOBIN | 79.8 | 2.2 | 59.7 | 5.2 | 59.4 | 5.5 | 75.0 | 3.2 | 99.8 | 5.3 | 87.5 | 2.6 | g/L | 90 - 150 |
| Hct | 0.2 | 0.0 | 1.8 | 1.6 | 0.2 | 0.0 | 0.2 | 0.0 | 0.3 | 0.0 | 0.3 | 0.0 | L/L | 0.27 - 0.45 |
| MCV | 33.1 | 0.7 | 33.2 | 0.8 | 33.3 | 0.8 | 33.0 | 0.7 | 32.3 | 1.1 | 27.7 | 0.6 | fl | 28 - 40 |
| MCH | 10.9 | 0.3 | 10.9 | 0.3 | 10.9 | 0.3 | 11.2 | 0.2 | 10.8 | 0.3 | 9.5 | 0.2 | pg | 8 - 12 |
| MCHC | 332.6 | 2.5 | 329.2 | 2.7 | 331.1 | 2.6 | 333.6 | 2.3 | 331.0 | 4.5 | 283.5 | 2.5 | g/L | 310 - 340 |
| WHITE CELL COUNT | 6.4 | 0.4 | 4.7 | 0.5 | 4.5 | 0.7 | 6.4 | 0.6 | 8.7 | 1.2 | 4.2 | 0.5 | $\times 10^9$/L | 4.0 - 12.0 |
| NEUTROPHILS | 2.1 | 0.2 | 1.7 | 0.4 | 1.7 | 0.5 | 3.0 | 0.5 | 5.1 | 0.9 | 1.1 | 0.2 | $\times 10^9$/L | 0.7 - 6.0 |
| LYMPHOCYTES | 3.9 | 0.3 | 3.0 | 0.3 | 3.2 | 0.4 | 3.2 | 0.2 | 3.4 | 0.6 | 2.8 | 0.4 | $\times 10^9$/L | 2.0 - 9.0 |
| MONOCYTES | 0.1 | 0.0 | 0.1 | 0.0 | 0.1 | 0.0 | 0.1 | 0.0 | 0.1 | 0.0 | 0.2 | 0.0 | $\times 10^9$/L | < 0.9 |
| FIBRINOGEN | 1.8 | 0.1 | 1.1 | 0.2 | 1.1 | 0.2 | 1.4 | 0.1 | 2.9 | 0.1 | 2.8 | 0.4 | g/L | 1.0 - 5.0 |
| BIOCHEMISTRY | | | | | | | | | | | | | | |
| SODIUM | 140.7 | 1.1 | 145.4 | 1.1 | 146.0 | 0.9 | 143.3 | 0.6 | 146.9 | 0.7 | 124.5 | 1.0 | mmol/L | 139 - 152 |
| POTASSIUM | 4.1 | 0.2 | 3.3 | 0.3 | 3.3 | 0.3 | 3.9 | 0.2 | 5.0 | 0.1 | 3.9 | 0.2 | mmol/L | 3.9 - 5.4 |
| CHLORIDE | 105.4 | 1.5 | 118.8 | 4.1 | 119.0 | 3.2 | 98.8 | 10.9 | 110.1 | 1.3 | 92.7 | 1.6 | mmol/L | 95 - 103 |
| BICARBONATE | 27.1 | 1.0 | 19.7 | 1.7 | 19.5 | 1.6 | 28.1 | 0.9 | 26.8 | 1.7 | 25.7 | 1.3 | mmol/L | 21 - 28 |
| Na/K | 35.3 | 1.6 | 48.7 | 6.1 | 47.4 | 4.7 | 37.7 | 1.8 | 29.3 | 0.8 | 26.5 | 1.0 | | > 24 |
| UREA | 4.0 | 0.2 | 3.4 | 0.4 | 3.4 | 0.3 | 4.2 | 0.3 | 5.6 | 1.2 | 2.6 | 0.2 | mmol/L | 2.8 - 7.2 |
| CREATININE | 78.9 | 4.1 | 73.1 | 6.2 | 75.8 | 6.0 | 83.6 | 3.4 | 136.6 | 28.0 | 69.2 | 4.4 | mmol/L | 70 - 170 |

| | | | | | | | | | (CONTINUED FROM FIG.10) |
|---|---|---|---|---|---|---|---|---|---|
| CALCIUM | 2.2 | 0.0 | 1.7 | 0.2 | 1.7 | 0.1 | 2.1 | 0.0 | 2.3 | 0.0 | 2.0 | 0.0 | mmol/L | 2.40 - 3.20 |
| PHOSPHATE | 1.5 | 0.1 | 1.2 | 0.1 | 1.2 | 0.1 | 1.5 | 0.1 | 1.9 | 0.2 | 1.5 | 0.1 | mmol/L | 1.61 - 2.35 |
| MAGNESIUM | 0.8 | 0.0 | 0.6 | 0.1 | 0.6 | 0.1 | 0.8 | 0.0 | 0.9 | 0.0 | 0.8 | 0.0 | mmol/L | 0.5 - 1.5 |
| GLDH | 11.6 | 2.0 | 7.2 | 1.1 | 7.8 | 1.2 | 10.2 | 1.8 | 8.0 | 1.4 | 7.3 | 3.3 | U/L | < 20 |
| B-OH BUTYRATE | 0.3 | 0.0 | 0.1 | 0.0 | 0.1 | 0.0 | 0.2 | 0.0 | 0.4 | 0.0 | 0.3 | 0.0 | mmol/L | < 0.9 |
| PROTEIN | 54.7 | 1.2 | 39.0 | 4.1 | 38.0 | 3.8 | 49.4 | 1.7 | 58.8 | 1.5 | 40.7 | 11.5 | g/L | 60 - 82 |
| ALBUMIN | 27.2 | 0.9 | 19.4 | 1.8 | 18.7 | 1.5 | 24.7 | 0.9 | 29.4 | 1.1 | 26.3 | 0.4 | g/L | 25 - 40 |
| GLOBULIN | 27.5 | 1.1 | 19.6 | 2.4 | 19.3 | 2.4 | 24.7 | 1.2 | 29.3 | 1.2 | 24.3 | 1.0 | g/L | 30 - 42 |
| T.BILIRUBIN | 1.2 | 0.1 | 0.8 | 0.2 | 0.7 | 0.2 | 0.8 | 0.2 | 0.4 | 0.2 | 1.0 | 0.5 | umol/L | < 9 |
| ALK. PHOS | 122.2 | 23.8 | 104.8 | 25.1 | 104.6 | 25.2 | 116.2 | 20.7 | 136.0 | 23.4 | 53.2 | 12.9 | U/L | 84 - 220 |
| GGT | 50.8 | 2.6 | 36.6 | 3.9 | 35.0 | 3.4 | 46.0 | 2.7 | 54.1 | 2.6 | 55.3 | 3.4 | U/L | 30 - 66 |
| AST | 80.6 | 3.9 | 60.0 | 6.3 | 60.2 | 6.6 | 60.2 | 6.6 | 139.9 | 10.8 | 99.5 | 11.4 | U/L | 53 - 153 |
| CHOL. | 1.6 | 0.1 | 1.1 | 0.1 | 1.1 | 0.1 | 1.4 | 0.1 | 1.5 | 0.1 | 1.5 | 0.1 | mmol/L | 1.3 - 2.0 |

FIG. 10A

SYSTEMS AND METHODS FOR LIMB TREATMENT

CROSS-REFERENCE TO RELATED APPLICATIONS

This application claims priority to and the benefit of U.S. Provisional Application Ser. No. 61/522,605, filed Aug. 11, 2011, entitled "Methods and Devices for Isolated Limb Treatment"; and U.S. Provisional Application Ser. No. 61/523,042, filed Aug. 12, 2011, entitled "Methods and Devices in Limb Retroperfusion Treatment"; the disclosures of which are hereby incorporated by reference herein in their entireties.

INTRODUCTION

The need for improved patient outcomes in the treatment of regional tissue diseases continues to drive innovative systems, agents, and therapies in targeted delivery of therapeutic agents and/or media to selected organs and anatomical structures. Systems and methods have been previously described that may target, as an example, coronary circulation from the rest of the body, allowing the delivery of therapeutic substances to ischemic or otherwise morbid tissue, as described in U.S. Patent Application Publication No. 2010/0274173, the disclosure of which is hereby incorporated by reference herein in its entirety. It is the intention of this application to further elucidate devices, systems and methods in the selective treatment of infectious, or otherwise morbid, limb tissue.

Over the next 20 years, it is projected that the number of people living with diabetes will double. During this period it is also expected that there will be a concomitant rise in the incidence of the complications of diabetes, including heart and blood vessel disease and lower limb infection. Diabetic foot/leg complications have an increasing level of severity depending on the stage of progression. In many cases, the first presentation is with advanced disease, which is accompanied by a high risk of lower limb amputation. Once a late stage infection can no longer be treated by conventional antibiotics, the treatment of last resort is limb amputation. The two-year mortality after lower limb amputation has been reported to be as high as 50%. In addition to the resultant disability, lower limb amputations are extremely costly to the healthcare system. In the United States, there are approximately 150,000 cases of moderate to severe diabetic foot infections per year, and this represents one of the leading causes for hospitalization for people living with diabetes. Most importantly, foot infections are the key indication for major lower limb amputation in 90% of people with diabetes. As such, it is estimated that up to 75,000 amputations occur annually in the U.S. in people with diabetes, and this accounts for approximately 65% of all lower limb amputations in the U.S. In Australia, there are approximately 3,500 amputations annually due to infective complications of diabetes.

While existing antibiotics are effective in treating the majority of milder infections, infections that are more severe (particularly those infections involving bone—i.e., osteomyelitis), fail to respond to standard treatment approaches. This results in the need for hospitalization and surgery, including major debridement and amputation. Standard therapies in this group of patients are often ineffective because adequate antibiotic levels cannot be achieved at the site of infection by simple oral or intravenous administration. Furthermore, co-existing complications (such as chronic kidney disease) render some more common drugs toxic or unable to be given in sufficient doses. As such, this group of patients represents the majority of those individuals who are admitted to hospital for management in Diabetic Foot Units. In these cases, surgical intervention (debridement and/or amputation) to address the infection and the ischemia may be required. Increasingly antibiotic-resistant infections of the diabetic foot are becoming more common. Specifically, Methicillin-Resistant Staphylococcus Aureus (MRSA) infections have been reported to present in significantly higher rates among diabetic individuals undergoing amputation as compared to those without amputation, further complicating wound healing and infection management.

Delivery of existing antibiotics by current means still results in treatment failures, as evidenced by the high rates of major amputation, or death. In the diabetic foot, treatment may be made difficult by numerous contributing factors, including (but not limited to) the anatomy of the foot; the often compromised blood supply to the region; the immunosuppression associated with diabetes; and, increasingly the nature of the infection with multi-drug resistant strains. Ultimately, treatment failure may be characterized by the failure to deliver, distribute and sustain therapeutic agents (i.e., antibiotics) in the infected tissue. Thus, management and cure of infections of diabetic wounds represent a significant unmet clinical need characterized by the complexity of the diabetic foot. Various techniques already have been described in the performance of: isolated limb infusion or perfusion, perfusion of the limb, and other superficial wound treatments. However, these techniques may be inadequate if used in the treatment of the morbid, diabetic limb.

Isolating a limb for the delivery of regional chemotherapy has been reported. In particular, limb isolation has been performed in patients with advanced melanoma or soft tissue sarcoma. During the procedure, cytotoxic agents are percutaneously infused through an arterial catheter with a syringe and regionally circulated for 15 to 20 minutes. The procedure is performed at low blood flow rates which are manually controlled, and in a non-normal hypoxic state. The low flow rates that increase the risk of thrombosis, coupled with the lack of sufficient oxygen to the limb, make this procedure unattractive for diabetic patients.

Isolating and chemically perfusing a limb has also been reported in the treatment of limb malignant melanomas. The performance of this procedure requires surgical immobilization via general anesthesia and placement of catheters using an invasive surgical cut-down technique into the major blood vessels, as near as possible to the tumor, and isolating the limb through the use of a tourniquet. Chemotherapy agents are then introduced to and removed from the tumor/target site. Upon completion of the chemotherapy treatment, the cut vessels are closed and the tourniquet removed before re-establishing circulation within the isolated limb. A less invasive procedure, with no general anesthesia, would provide an enormous benefit.

Venous perfusion of the limb with antibiotics (for osteomyelitis or other chronic infections) has also been reported. This method utilizes a selective pressure technique, in combination with antibiotics that are introduced through an intravenous catheter to the focus of infection. A pressure dressing is placed over the target area and a proximal tourniquet is placed. The antibiotics are delivered to the target site via venous flow that may be shunted into the deep venous system and into the bone. Notably, this technique delivers an antibiotic venously, with no regard to its removal nor continued circulation within the limb during treatment. Although the technique may be relatively simple and provide for more effective delivery of antibiotics (i.e., selective versus systemic injection), it is often limited in its use due to a lack of appropriate access vessels in many patients, no provision for limb oxygenation, and the confounding effects of concomitant venous disease in patients.

Treatment of superficial wounds has also been reported in clinical literature although the various techniques do not address deep-seated infection. Moreover, other techniques described to treat limbs do not generally allow for selective antibiotic treatment.

SUMMARY

At present, there are no devices in routine clinical practice that enable sustained high doses of appropriate antibiotics and/or other therapeutic drugs to be specifically administered to the leg of individuals with foot infections, while maintaining oxygenation of the limb and providing the capacity to minimize exposure of the rest of the body to the potentially adverse effects of the drugs (e.g., in patients with diabetic nephropathy). The devices and systems described herein provide for selective delivery of drugs and/or antibiotics in a sustained, high local concentration to ischemic/edemic/necrotic/morbid tissue in a minimally invasive and effective manner. It is believed that the use of these devices, systems, and methods in performance of an earlier, more aggressive, therapeutic (i.e., antibiotic) intervention may treat and/or prevent lower limb infection and morbidity.

In this context, the devices and systems described herein may be used to therapeutically intervene with selective administration of high dose antibiotics (with or without oxygenated perfusion) to morbid limb tissue, thus improving clinical outcomes (reduce amputation rates, promote wound/tissue healing, reduce hospitalization length of stay, and generally improve quality of life). A patient benefiting from the therapies described herein may have concomitant therapies to address an acute occlusion that might, among other things, include surgery (harvested blood vessel or graft used to bypass the occlusion), balloon angioplasty, stenting, and/or atherectomy.

In one aspect, the technology relates to a method of delivering a medicament to a limb of a patient body, the method including: isolating a circulatory system of the limb from a circulatory system of the patient body, wherein the limb circulatory system includes substantially all limb arteries and substantially all limb veins located between an isolation region and an end of the limb; inserting a perfusion catheter into a limb artery of the limb circulatory system in an antegrade position; inserting a collection catheter into a limb vein of the limb circulatory system in a retrograde position; circulating substantially all of a blood flow of the limb circulatory system by collecting the blood flow with the collection catheter and delivering the blood flow with the perfusion catheter; and perfusing a medicament to the limb circulatory system with the perfusion catheter. In an embodiment, the isolating operation includes applying a tourniquet to the limb. In another embodiment, the isolating operation includes expanding an occlusion device surrounding the perfusion catheter and expanding an occlusion device surrounding the collection catheter. In yet another embodiment, the method further includes expanding a support structure within the limb artery, prior to the circulating operation. In still another embodiment, the support structure includes a plurality of expandable members, wherein the expandable members are located at least partially within the collection catheter during the inserting step.

In another embodiment of the above aspect, the support structure includes a plurality of expandable members, wherein the expandable members are located both internal and external to the collection catheter during the inserting step, and wherein at least one expandable member is secured to a distal end of the collection catheter. In an embodiment, the circulating step is performed with a pump located external to the patient body. In another embodiment, the method further includes at least one of oxygenating the blood flow and heating the blood flow. In yet another embodiment, the medicament includes at least one of antibiotics, anti-thrombin agents, anti-platelet agents, anti-spasm agents, and thrombolytic agents, and may also be Timentin. In still another embodiment, the pump circulates the blood flow at a rate of about 200 ml per minute to about 300 ml per minute.

In another aspect, the technology relates to a method of delivering a medicament to a limb of a patient body in a retrograde orientation, the method including: inserting a perfusion catheter into a limb vein of the limb circulatory system in a retrograde position; inserting a collection catheter into a limb artery of the limb circulatory system in a antegrade position; isolating a flow of blood within the limb from a flow of a systemic flow of blood; circulating substantially all of a blood flow of the limb circulatory system by collecting the blood flow with the collection catheter and delivering the blood flow with the perfusion catheter; and perfusing a medicament to the limb circulatory system with the perfusion catheter. In an embodiment, wherein the perfusion catheter includes a selectively expandable occlusion member substantially surrounding the catheter, and a delivery end located distal from the occlusion member. In another embodiment, the delivery end defines a plurality of openings. In yet another embodiment, the step of inserting the perfusion catheter includes spanning a plurality of venous valves with the delivery end of the perfusion catheter. In still another embodiment, the delivery end includes a spring. In another embodiment, the selectively expandable occlusion member is movably displaceable along the delivery end of the perfusion catheter. In still other embodiments, the selectively expandable occlusion member is located on the delivery end of the perfusion catheter so as to at least partially occlude at least one of the plurality of openings of the delivery end of the perfusion catheter.

BRIEF DESCRIPTION OF THE DRAWINGS

There are shown in the drawings, embodiments which are presently preferred, it being understood, however, that the technology is not limited to the precise arrangements and instrumentalities shown.

FIGS. 10 and 10A depict clinical pathology data for a test sample.

DETAILED DESCRIPTION

The following describes systems and methods in providing therapeutic therapies in a targeted and aggressive manner, aimed at achieving more effective tissue dosing rates for infection control. The system and methods described herein may be referred to in the context of percutaneous isolating limb perfusion (PILP), although the systems and methods may be utilized for isolating portions of limbs or other parts of the body. This system also allows the use of antibiotics that previously could not be used because of their systemic toxicity. It is also anticipated that this delivery may also include the perfusion of the treated tissue with oxygenated blood. The oxygenation system may, among other things, provide for selective and sufficient oxygenation of the blood (resolution of ischemia/edema), and removal of carbon dioxide or other toxins. Notwithstanding the versatility of the techniques described herein, for clarity, examples used in this application will refer to PILP systems and PILP procedures performed in an isolated, diabetic (or otherwise morbid) limb.

Figure 1:
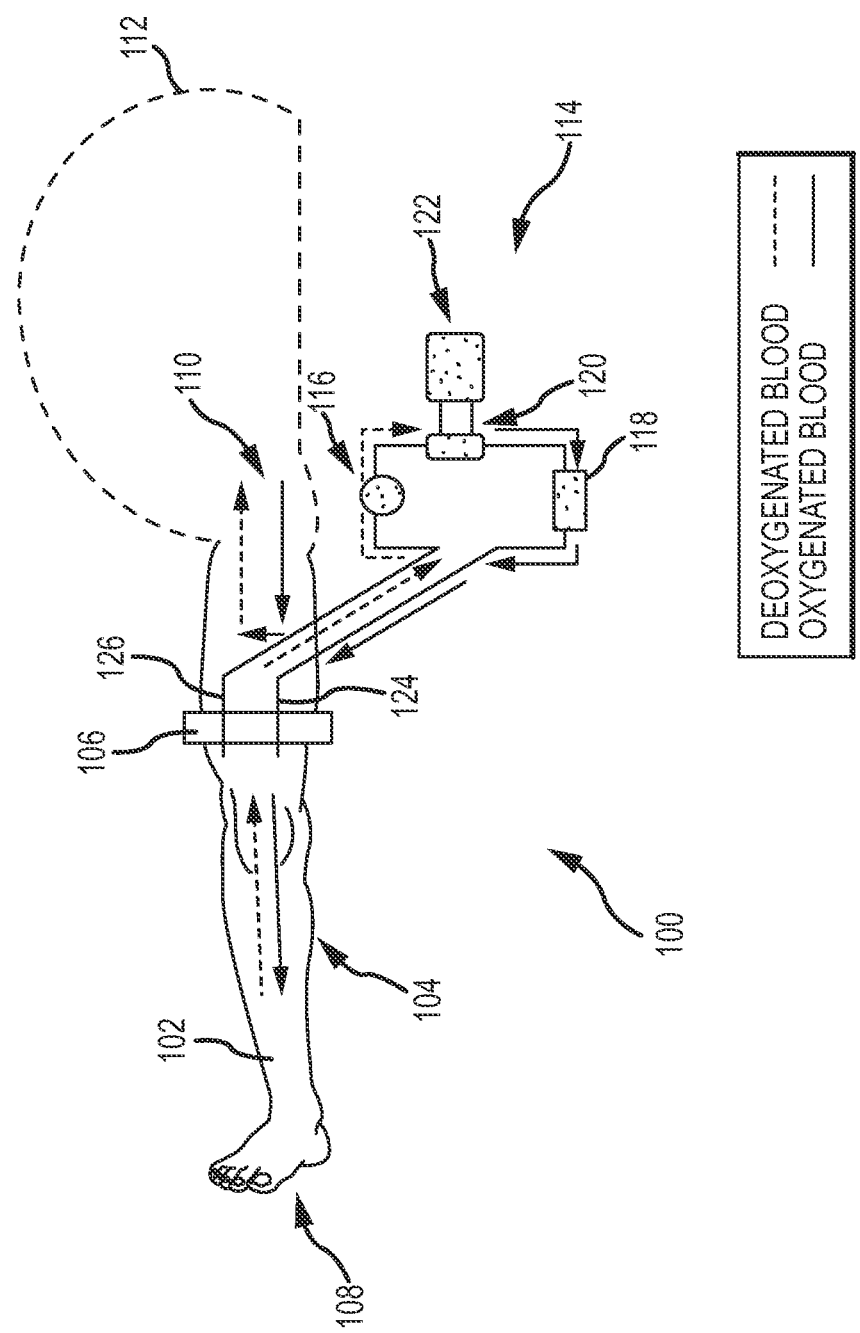
FIG. 1 depicts a system for treating a morbid limb.

FIG. 1 depicts a system 100 for treating a diabetic limb 102. Two circulatory systems are depicted. The first is a circulatory system 104 of the diabetic limb 102. This limb circulatory system 104 includes substantially all of the arteries and veins located between an isolation element 106 and an end 108 of the limb 102, in this case, a foot. These veins and arteries may be referred to as being "below" the isolation element 106. The second circulatory system is a systemic circulatory system 110 that includes substantially all of the remaining arteries and veins on the opposite side of the isolation element 106, and may be referred to as being "above" the isolation element 106. As can be seen, both circulatory systems 104, 110 circulate oxygenated blood (via the arteries) and deoxygenated blood (via the veins). In the systemic circulatory system 110, the blood may be oxygenated through a normal circulation process that utilizes the heart and lungs of the patient 112. The limb circulatory system 104 is connected to an extracorporeal circuit 114 that includes a pump 116, a perfusate or medicament reservoir 118, an oxygenator 120, and an optional heater 122 or other elements. A plurality of catheters 124, 126 connect the extracorporeal circuit 114 to the limb circulatory system 104.

Figure 2:
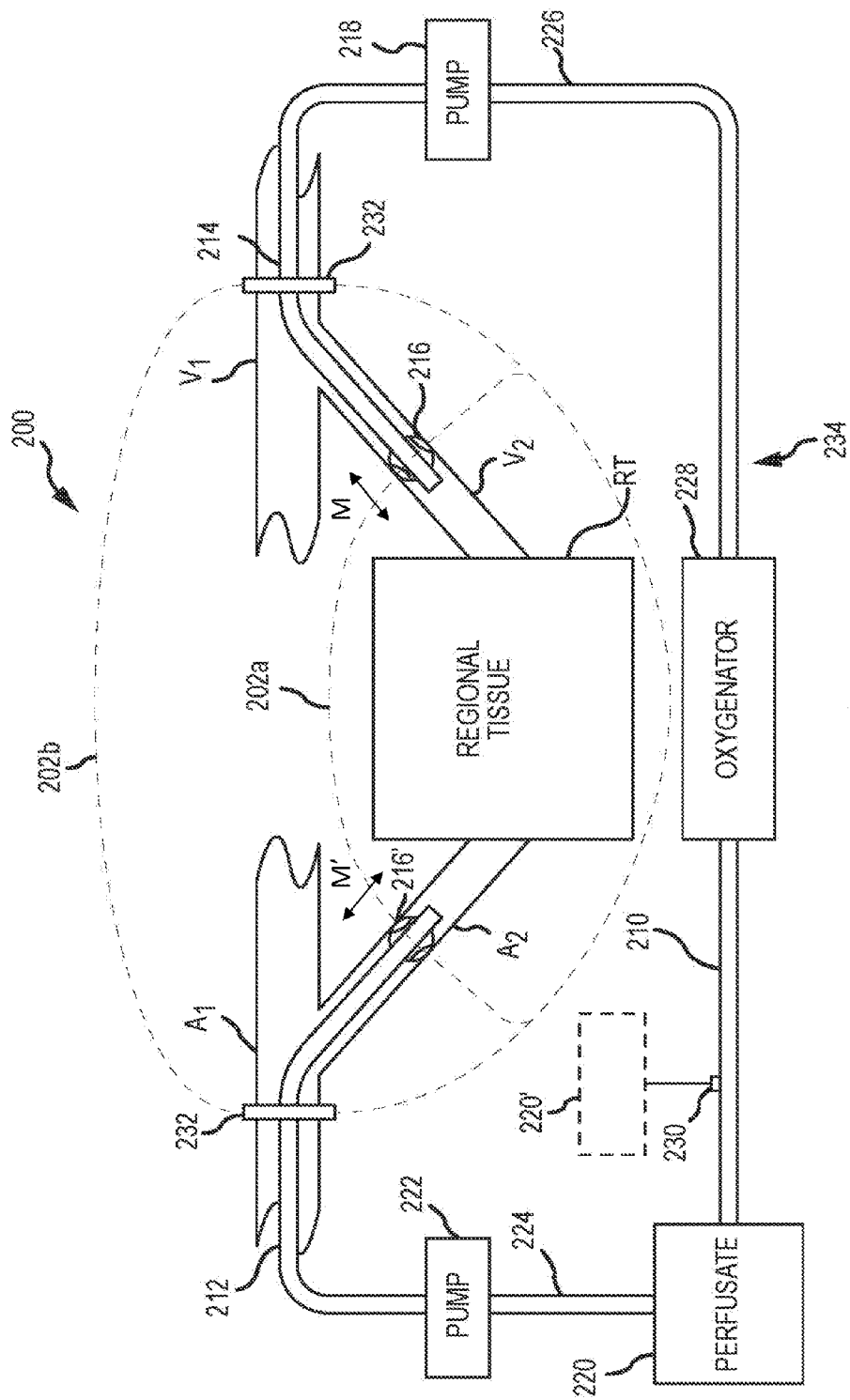
FIG. 2 depicts a system for treating a morbid limb.

Another PILP system 200 is depicted in FIG. 2, which includes a limb 202 that includes a number of arteries A and veins V, as well as regional tissue RT (i.e., the tissue intended to be treated). More specifically, FIG. 2 depicts a major artery A1 and a smaller branch artery A2 for supplying oxygenated blood to the regional tissue RT, and a major vein V1 and a tributary vein V2 for directing blood away from the regional tissue RT. The use of larger (A1 and V1) and smaller vessels (A2 and V2) as depicted is illustrative of the variety of locations may be treated by the PILP system 200. In general, the treatment performed is intended to be isolated to the limb 202. None of the disclosure herein should be construed as to require only large or only small vessels in the treatment. As an example, it is contemplated that vessel sub-selection may be difficult to perform if, for example, access to a smaller vessel is impracticable. In this case, a larger vessel intubation may be required.

During a PILP procedure, arterial perfusion and venous collection catheters are positioned respectively into the artery and vein that predominantly satisfy blood flow to the limb 202. Isolation of the circulatory system of the limb 202 may be performed in a number of ways. For example, an occlusion member 216 (and/or vacuum placed on the venous vessel wall with a collection pump 218), may be located on the venous collection catheter 214. The occlusion member 216 is located proximally from the tip of the catheter 214, and is located a sufficient distance from the tip of the collection catheter 214 so as to allow placement of the tip as required. Additionally, an occlusion member 216' on the arterial perfusion/infusion catheter system 212 may be similarly utilized to isolate arterial flow to the region of tissue to be treated. Both of these occlusion members 216, 216' may be actuated manually or automatically upon activation of the re-circulation system (pumps, oxygenator, heater, etc.). Alternatively, isolation of the limb from systemic circulation can be achieved through application of a tourniquet 232 (pneumatic or manual) appropriately applied to the limb 202 with approximately 40 mm Hg of pressure, for example. In FIG. 2, occlusion members 216, 216' may be located in smaller vessels (A2 and V2), thus reducing the total volume of the limb circulatory system 202a. FIG. 2 also depicts placement of a tourniquet 232 that isolates the limb circulatory system 202b, such that it has a larger blood volume.

Activation of a pump 222 provides for re-circulation of blood and agents through the extracorporeal circuit 234. It should also be noted that the occlusion members 216, 216', if present, may be attached on the delivery catheter 212 and the collection catheter 214 at preset distances, or be constructed so as to move along the catheters independently of the location of the tip of the catheter. The activation of the occlusion members 216, 216' may be hydraulically performed by a medium, such that the medium fills the occlusion member (e.g., a balloon) or the occlusion members 216, 216' could be mechanically actuated to cause expansion of the member 216, 216' radially of the catheter.

Collection 214 and perfusion 212 catheters represented in the drawings illustrate the use of a single distal perfusion/ collection port, although multiple port and port locations along the distal regions of the catheters 212, 214 may provide optimal perfusion/collection, and may be varied based on treatment location. It is anticipated that the flow through the extracorporeal circuit 234 and regional tissue RT may be about be 200 to about 300 ml per minute, although the flow could be significantly higher or lower depending on several factors, such as size of limb, disease state, etc.

In FIG. 2, a reservoir of a perfusate or medicament is shown at 220. The perfusate can be any therapeutic agent selected for the treatment of ischemic, infected or otherwise diseased limb tissue. By way of example, suitable agents for use in the PILP systems depicted herein are antibiotics, anti-thrombin agents, anti-platelet agents, anti-spasm agents, and thrombolytic agents. In the treatment of limb tissue infection, the use of antibiotics is of particular interest as a therapeutic agent. The delivery pump 222 draws the perfusate from the reservoir 220 through tubing 224 and delivers the perfusate to the perfusion catheter 212. Tubing 226 connects the output of the collection pump 218 to an oxygenator 228. The oxygenator 228 can be any commercially available unit for exchanging oxygen for carbon dioxide contained within blood, in addition to heating the blood. In the embodiment of FIG. 2, the perfusate reservoir 220 receives blood from the oxygenator 228 for recirculation through the circuit 210. The perfusate reservoir 220 of FIG. 2 may be also be configured as a location upon the connecting tubing between the oxygenator 228 and the delivery catheter 212 that is capable of receiving a medicament there through. For example, a medicament delivered through the wall of the tubing with a syringe and needle may be utilized. Furthermore, introduction of the medicament into the perfused blood at the proximal hub of the delivery catheter is also contemplated.

In an alternative embodiment, pump 222 and reservoir 220 could be eliminated and blood may be delivered from the oxygenator 228 directly to the perfusion catheter 212. In that case, perfusate could be added to the tubing 210 through needle injection or intravenous drip or the like from a reservoir 220' into a port 230. With the embodiment of FIG. 2, a higher dose or concentration of the perfusate than otherwise be administered safely through delivery to the entire body of the patient is administered directly only to the morbid limb circulatory system 202.

It may be necessary, in some circumstances, to balance the flow of blood and perfusate between the collection portion of the system 200 and the perfusion portion of the system 200. In such a case, a collection reservoir (not shown) may be placed at a location along the tubing circuit between the collection catheter and the oxygenator so as to provide a buffer between the collection and the perfusion of blood and perfusate into the limb 202.

Figure 3:
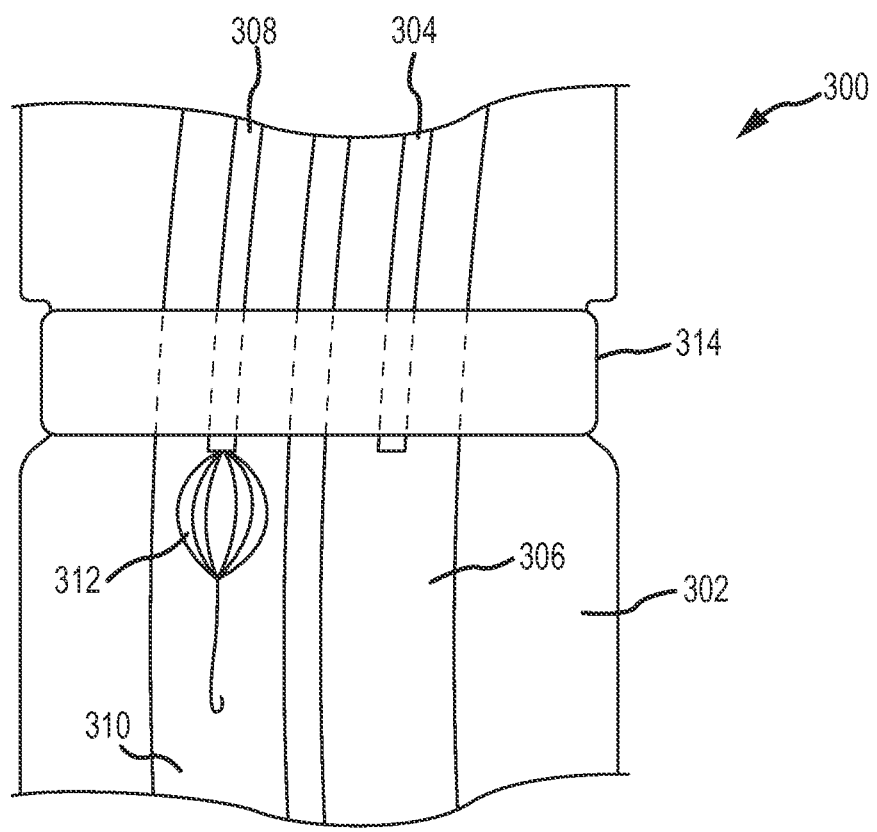
FIG. 3 depicts an isolation system for a morbid limb treatment system.

FIG. 3 depicts an enlarged partial view of an exemplary isolation system 300 for a limb treatment system. Such treatment of the limb 302 may include placement of an arterial perfusion or infusion catheter 304 into a femoral artery 306, positioned antegrade (i.e., the catheter 304 directed from the groin towards the foot). Additionally, a venous return or collection catheter 308 may be placed retrograde in a femoral vein 310 (catheter 308 travels from the groin to the foot). A support device 312 may be located at least partially within the lumen of the collection catheter 308 prior to its use for vessel support. Subsequently, support device may be expanded during use. Support device 312 may also be secured, or otherwise attached near the distal tip of the collection catheter 308. The venous support device 312 may prevent the collapse of the major vein 310 which experiences significant negative pressure upon activation of the pump. Exemplary support devices are known in the art, for example, as described in the U.S. Patent Application Publication No. 2009/0018526, the disclosure of which is hereby incorporated by reference herein in its entirety. Other acceptable types of support systems are described below. The limb circulatory system may be isolated from the corporal blood supply system by applying an external tourniquet 314 around the limb 302, in proximity to distal portions of the catheters 304, 308. In this configuration, flow to or from the lower portion of the limb 302 may be circulated via inserted catheters 304, 308. Activation of the pump draws venous blood out of the vein 310 and drives oxygenated blood (and treatment agent) into the limb 302 through the perfusion/infusion catheter 304. Although the above example includes the application of a tourniquet 314, other exemplary system configurations to perfect the isolation and perfusion may include systems that have inflatable or otherwise expandable elements to cause occlusion within the selective vasculature, as described previously in FIG. 2.

Figure 4A:
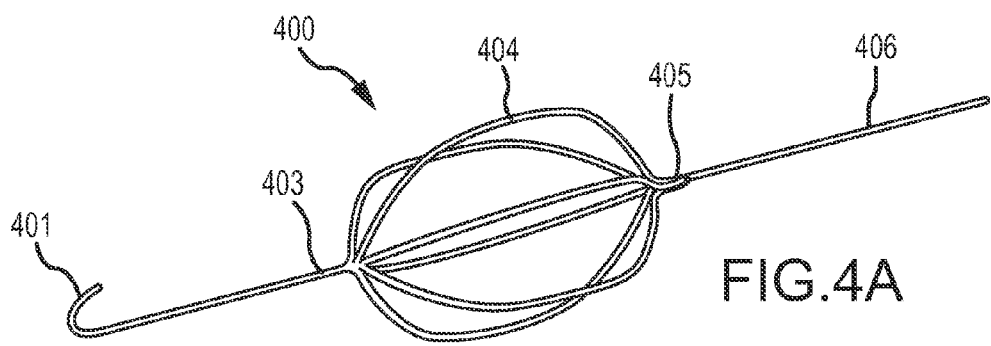
FIGS. 4A-4C depict a support system for a catheter.
Figure 4B:
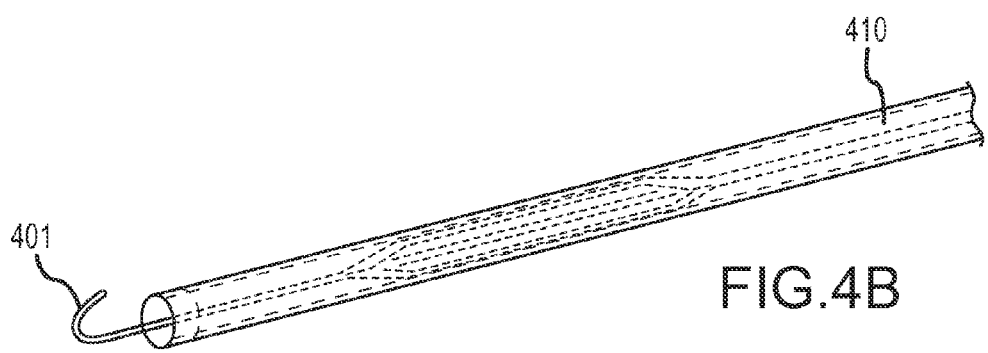
Figure 4C:
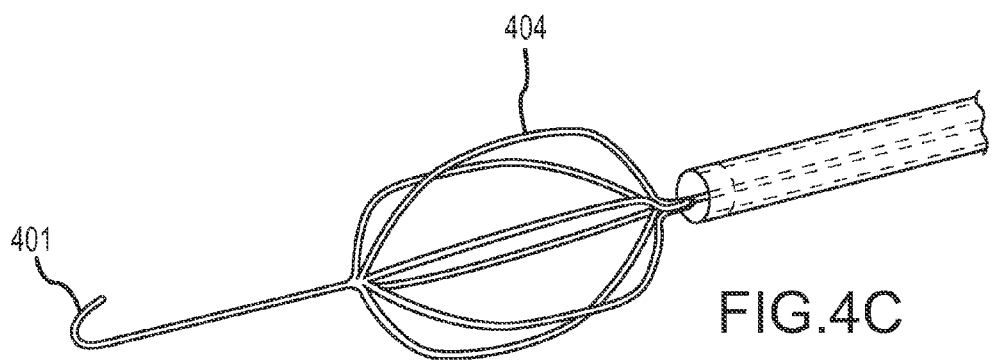

FIG. 4A depicts an example of an expandable member 400, in its expanded condition, suitable for supporting a vessel. Expandable member 400 is provided in the form of an expandable framework 404 and is adapted to be percutaneously deliverable to the blood vessel in a collapsed condition. FIG. 4B shows the expandable member 400 in a collapsed condition within a catheter 410, in which ends 403, 405 have been drawn apart to radially reduce the member. When collapsed within catheter 410, an atraumatic tip 401 may protrude from the catheter 410 to assist in guiding the support device into the vessel prior to deployment. When the expandable member 400 has been guided into the target blood vessel, the catheter 410 is retracted (or the expandable member 400 is pushed out of the catheter 410), deploying the member 400 into the vessel where it expands. FIG. 4C shows the expandable framework 404 fully deployed from the catheter 410, with the expandable member 400 in its fully expanded condition.

A guidewire or stem 406 extends within the catheter 410 and is used to deliver the expandable member 400 from a point of entry through the peripheral vasculature to the target vessel. Atraumatic tip 401 coupled to the expandable member 400, is adapted to make atraumatic contact with vessel walls during placement of the device by deforming or deflecting off the vessel wall on contact. This can be achieved by incorporating flexibility into the tip 401 so that it deforms upon contact with the vessel wall. Alternatively or additionally, the tip may be shaped or curved to avoid trauma.

Figure 4D:
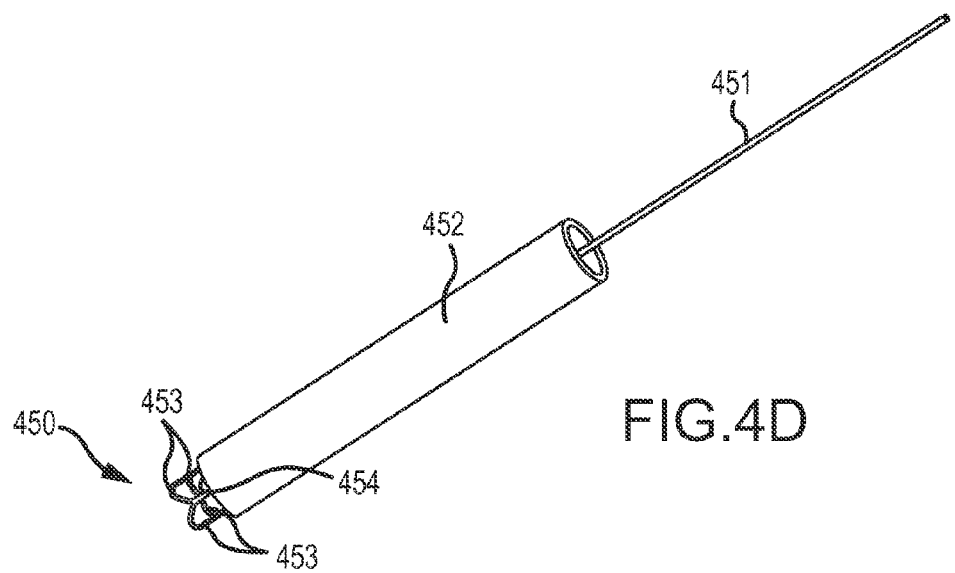
FIGS. 4D-4E depict another support system for a catheter.
Figure 4E:
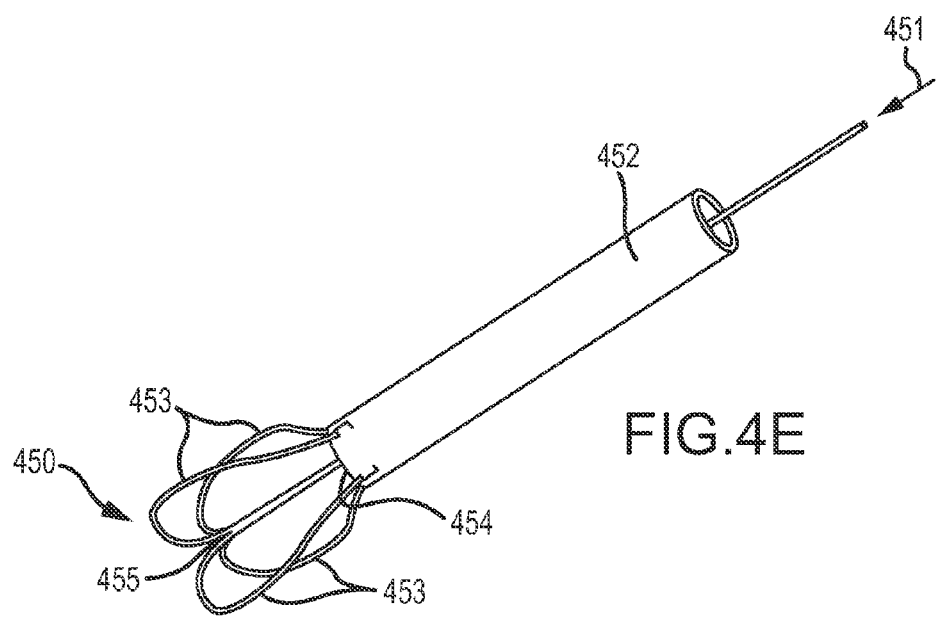

Referring now to FIGS. 4D and 4E, another example of a support device 450 is shown. A lumen 452 has a control stem 451 extending therein. Four loop portions 453 are provided. Each loop portion is attached at a first loop end to a distal end 454 of the lumen, and at a second loop end to the control stem at junction 455. The loop portions 453 are controllably expandable by advancing the control stem 451 within the lumen 452 in the direction shown by arrow 456 (FIG. 4E). The support device 450 is percutaneously deliverable with the plurality of loop portions 453 housed substantially within the lumen 452 as illustrated in FIG. 4D and expandable as illustrated in FIG. 4E.

Figure 5:
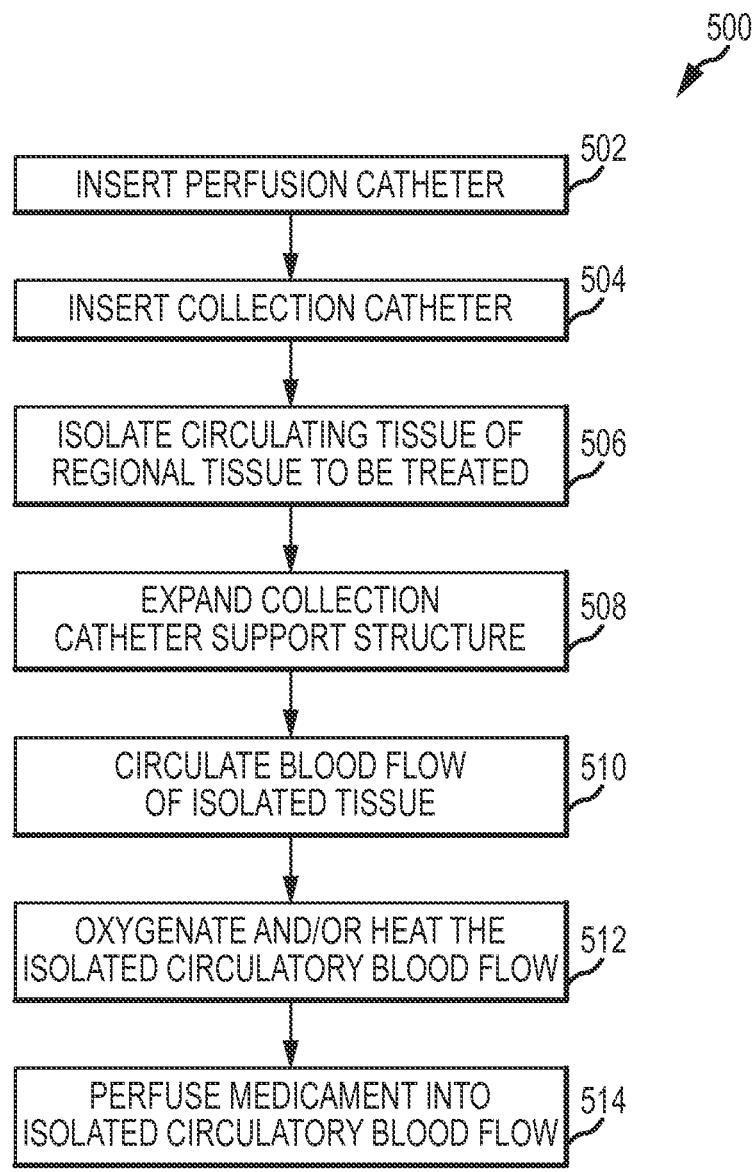
FIG. 5 depicts a method of delivering a medicament to a morbid limb of a patient body.

FIG. 5 depicts a method 500 of delivering a medicament to a limb of a patient body. Typically, the perfusion catheter and collection catheter are first inserted as required into the limb (operations 502, 504). The circulatory system of the limb is then isolated (operation 506). As described above, this may be performed by occlusion elements on the catheters or by application of a tourniquet to the limb, proximate the distal portions of the catheters. If desired, a support structure of the collection catheter system may be expanded, or otherwise deployed (operation 508), to support the vein during the collection process. Thereafter, circulation of the blood flow may begin (operation 510). This includes collecting the blood flow with the collection catheter and delivering the collected blood with the perfusion catheter, for example, with the systems described above. During circulation, the blood flow may be heated and/or oxygenated (operation 512). Medicament may be perfused into the circulating blood flow (typically after oxygenation, prior to perfusion back into the isolated circulatory system) in order to provide the desired treatment (operation 514).

It should be noted that, although the descriptions have illustrated the application of the delivery devices principally through the femoral artery and veins, the access for the treatment could be performed through other vessels, including by way of example: superficial, iliac, popliteal, tibial, and dorsal arteries; and the saphenous, popliteal, tibial, and fibular veins. In addition, the access sites may be ipsilaterally or contralaterally positioned to the distal ends of the delivery or collection catheters. The location of the access points and delivery devices may vary depending on, among other things, the location of the ischemic/infected tissue to be treated, the blood flow and pressures in the treatment region, concentration of treatment media, and ability to access vasculature(s). Moreover, morbid tissue residing in other regional areas of the body may require alternative access and delivery sites to effectively treat, and it is not intended that the devices, systems and methods described herein should be limited to lower limb salvage. By way of example, the systems and therapies described could be advantageously applied to morbid tissues of the kidneys, liver, spleen, gastrointestinal system, etc.

Figure 6:
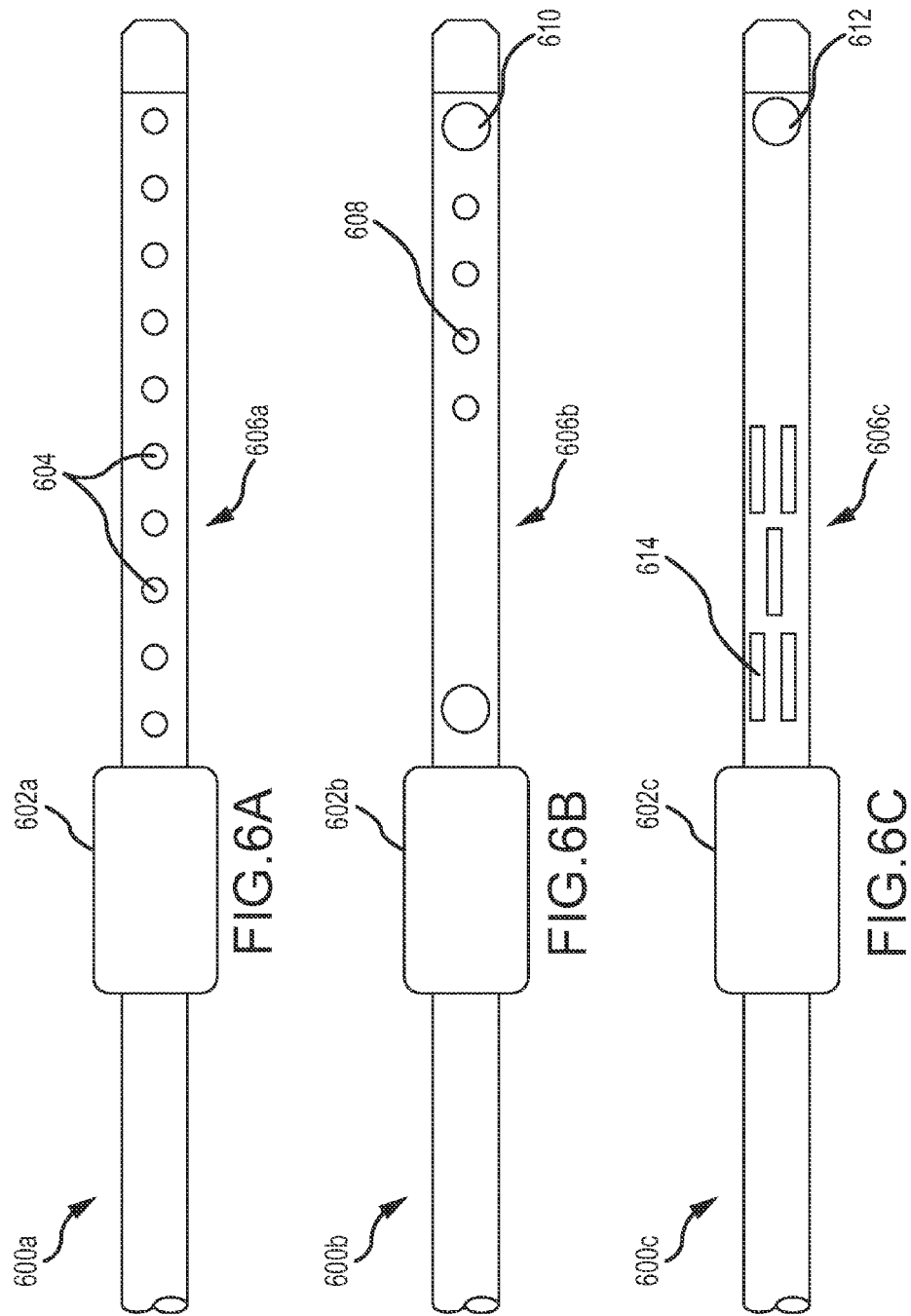
FIGS. 6A-6C depict retrograde perfusion catheters.
Figure 7:
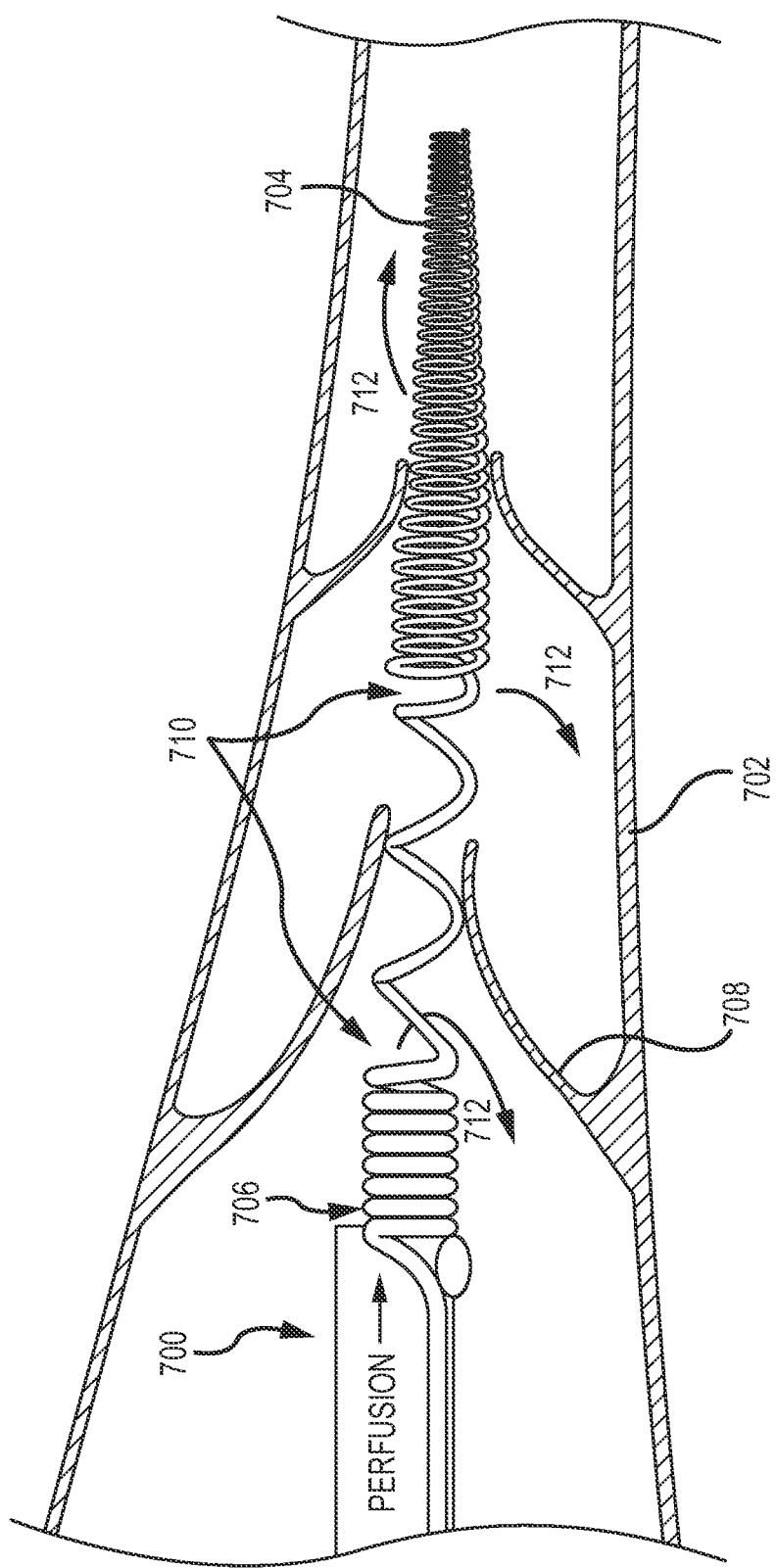
FIG. 7 depicts a device for retrograde perfusion in a vein.

An alternative embodiment of the systems depicted in FIGS. 1-3 is depicted in FIGS. 6A-7. In the alternative embodiment, perfusion of the limb may be performed in a retroperfusion procedure with concomitant devices and systems. In embodiments utilizing retroperfusion, the general system shown in FIG. 2 may be operated in reverse, providing perfusion and infusion to the venous vasculature, while draining/collecting blood/perfusate from the arterial vasculature.

Such "reverse perfusion" may have clinical/therapeutic advantages however it has not been practiced on the lower limbs for a number of reasons. As an example, the presence of venous valves may prevent insertion of catheters and other instruments venously. Further, once placed into a region of a valved vein, the delivery of a medicament/perfusate to the region (i.e., through a single delivery port of a delivery catheter) would be limited to the region between the valves of the vein. Other problems with retroperfusion are also known to those of skill in the art.

One clinical advantage of retroprofusion is that perfusate can be introduced venously, thus avoiding the inherent complications of arterial perfusion of a vascular bed that may have significant and diffuse atherosclerosis. Occluded vascular beds (due to atherosclerosis, for example) can greatly limit fluid flow, making arterial perfusion difficult. In addition, atherosclerosis of the arterial walls may diminish the effectiveness of nutrients and medicaments through the vessel wall to target tissue. Retroperfusion may overcome these challenges in providing perfusion and/or medicaments in treatment of morbid tissues.

With general reference to FIG. 2, the venous catheter 214 would function as the delivery catheter to vein V2 and the arterial catheter 212 collects the blood and perfusate/medicament from artery A2. The devices and systems used in the performance of arterial PILP may be modified so as to perform retroperfusion. For example, although the catheters 212 and 214 depicted in FIG. 2 are described, in one embodiment, as having a single distal opening, venous introduction of blood and therapeutic agents (e.g., a drug, cell, gene therapy, protein, antibiotic, etc.) would be constrained with the use of a delivery device comprising a single, distal outlet port. As described above, this is because the venous vasculature has valves that may retard delivery of perfusate to regions outside of the valved area of the vein.

Venous perfusion catheters to overcome this impediment are depicted in FIGS. 6A-6C. Each catheter 600a-600c includes multiple ports along the length thereof, which may be laser cut, machined, or otherwise formed in the wall of the perfusion catheter. Each catheter 600a-600c includes an occlusion member 602a-602c about the catheter 600a-600c. In FIG. 6A, the catheter 600a includes a number of evenly-spaced, similarly-sized holes 604, through a delivery end 606a of the venous delivery catheter 600a that administers perfusate to provide sufficient perfusion to the selected region. FIG. 6B depicts a delivery end 606b having both small 608 and large 610 holes for the delivery of perfusate. These holes 608, 610 may be located as required or desired for a particular application. Another embodiment is depicted in FIG. 6C, where a catheter delivery end 606c includes both holes 612 and slots 614. Again, these may be located and sized as required or desired for a particular application. In the depicted embodiments, the occlusion members 602a-602c are part of the respective perfusion catheter 600a-600c. In alternative embodiments, the occlusion member may be part of a separate catheter/elongate member (e.g., guide, tubular guidewire) than the delivery catheter which is used to deliver perfusate. In such a case, the occlusion member would reside and function independent of the perfusion catheter, on a distal portion of a catheter/elongated member. One advantage of such of a construction may be to allow a multitude of "delivery port" lengths to accommodate various venous architectures. Advantageously, the occlusion member may be placed so as to allow only selected ports to be available for perfusion delivery. In this case, the length of occlusion member 602 along the delivery catheter 600 may be long enough to occlude some, or all, of the delivery ports, if warranted.

In an alternative embodiment, depicted in FIG. 7, a perfusion catheter 700 is located within a vein 702, which could be vein V1, as identified in FIG. 2. The perfusion catheter 700 includes a distal, elongate, elliptical member, such as a spring 704. The spring 704 may extend from an end 706 of the catheter 700 and may be of a length sufficient to extend across several venous valves 708. The spring 704, by its coiled nature, may include a number of portals 710 (e.g., extended spaces between the coils) to introduce perfusion (identified by arrows 712) while providing a scaffold for introduction of perfusion across the valves 708. Device 700 may also work in combination with an occlusion member (not shown), such as those described herein or those depicted in FIG. 6A-6C.

Figure 8:
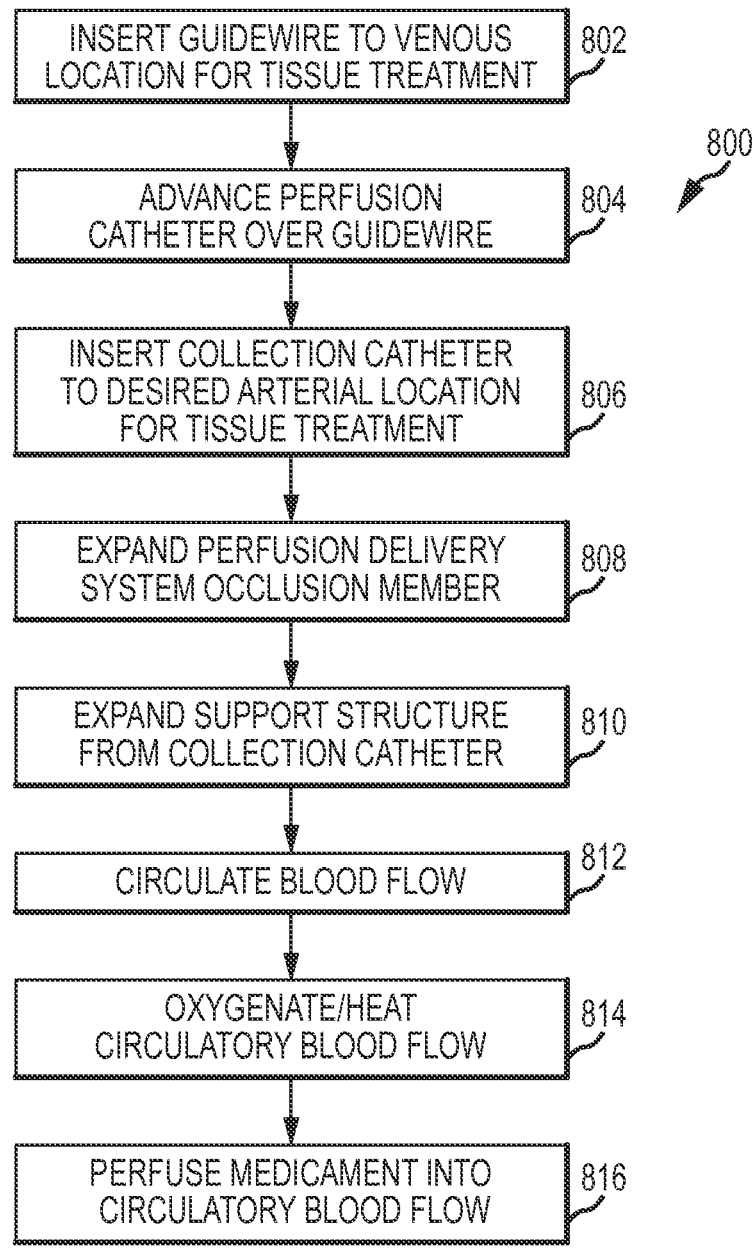
FIG. 8 depicts a method of retrograde delivery of a medicament to a morbid limb of a patient body.

A method of performing retrograde perfusion 800 is depicted in FIG. 8. A guidewire may first be inserted into a desired venous location within the isolated leg (operation 802). This may include spanning a number of venous valves retrogradely from the femoral vein with the guide wire. In one embodiment, this may be accomplished with known vein stripping procedures that are typically used for the treatment of varicose veins. A guidewire may be passed from the groin, into the leg, and across the valves. Thereafter, a perfusion catheter, such as the types depicted in FIGS. 6A-6C, may be advanced into the lower limb, over the guidewire (operation 804). The perfusion catheter may be advanced through a separate guide catheter, or may already be inserted within the guide catheter, such that the guide and perfusion catheter may be inserted into the vein simultaneously. A collection catheter may be introduced, in some cases via the femoral artery, to a desired location within the limb (operation 806). The guide catheter, the perfusion catheter, or a separate elongate member may include an occlusion element, balloon, or other expandable element that may be expanded to occlude the vein (operation 808) prior to perfusion. Venous occlusion may be performed proximate, higher, or lower than the knee, if desired. Prior to initiating circulation, a delivery system occlusion member and a collection catheter support structure may be expanded (operations 808 and 810, respectively). Thereafter, circulation of the blood flow may begin (operation 812). This includes collecting the blood flow with the collection catheter and delivering the collected blood with the perfusion catheter, for example, with the systems described above. During circulation, the blood flow may be heated and/or oxygenated (operation 814). Medicament may be perfused into the circulating blood flow in order to provide the desired treatment (operation 816). In an embodiment of the method, the therapeutic agent flow to the lower limb may be about 200 ml/min to about 300 ml/min, but other flow rates are contemplated.

One promising, exemplary therapeutic agent for delivery to infected regional limb tissue (in addition to the extracorporeal perfusion) includes the antibiotic Timentin, marketed by GlaxoSmithKline. Preliminary, pre-clinical animal studies utilizing Timentin with a PILP system such as that described herein have been performed. Timentin concentrations equal to or higher than those expected to be achieved in humans (per Liquid Chromatography Mass Spectrometry assay analysis, as discuss in the Example below) revealed no significant hematological, biochemical, or histological impact observed acutely or chronically.

In use, Timentin can be administered via a PILP system in conjunction with the perfusion/infusion catheter. It is anticipated that the serum concentration of Timentin in the body while using the PILP circuit could be equal to, or less than, concentrations observed when Timentin is administered intravenously (systemically), at about 300 µg/ml. However, it is also anticipated that the Timentin concentration within the region of treatment (RT) could be higher while using the PILP circuit since a higher concentration can be isolated to the region, and not pass systemically. The dosage, and concentration to be administered to the circuit, may vary significantly depending on limb volume, circuit volume, flow rates, volume of tissue to be treated, disease state, and other factors.

It is anticipated that the re-circulating isolated limb perfusion may be provided over an extended period of time, or could be performed multiple times for shorter durations. The variability may relate to many factors such as disease extent, disease state, patient tolerance, dosing of therapeutic agent, therapeutic agent activity, etc. It is believed that one such therapeutic regimen for PILP with antibiotic Timentin (including perfusion) might be multiple therapies performed over several days (once per day), with each procedure being performed for about 30 minutes. At the end of each treatment, the pump would be turned off, the occlusion member(s) (or tourniquet) deactivated, the arterial and venous catheters removed, and the circuit contents re-introduced into the systemic circulation.

Example

Delivery of Timentin Using PILP in a Large Animal Model

The antibiotic Timentin (composed of ticarcillin sodium and potassium clavulate) was administered to the hind limb of sheep using a Percutaneous Isolated Limb Perfusion procedure (PILP) at the dose administered systemically in the clinical setting, to evaluate the safety of the antibiotic.

Method

A total number of 10 crossbred sheep were used for this study. Under general anesthesia (induction, 2 mg/kg propofol; maintenance, isoflourane 2% in oxygen), vascular sheaths were placed in the carotid artery and jugular vein to allow positioning of balloon catheters in the femoral artery and vein of the sheep under fluoroscopic guidance. The support device was placed in the femoral vein catheter and the PILP system connected to capture venous blood which is oxygenated with a membrane oxygenator. The re-oxygenated blood is then returned to the femoral artery via a roller pump. In the sheep model, balloon catheters were employed to isolate the limb vasculature to overcome the anatomical difficulties of positioning a tourniquet effectively.

Once the PILP circuit was established, a bolus dose of Timentin (620 µg/ml, equivalent to the initial systemic dose of 3.1 g achieved in a 70 kg patient) was delivered to the limb via the circuit. This was followed by a continuous infusion of Timentin (2480 µg/ml for the length of the infusion, 30 min) into the circuit to maintain a concentration of ~600 µg/ml within the circuit to compensate for any leakage from the system as a consequence of using balloon catheters instead of a tourniquet system.

Recirculation was maintained for 30 min during which time blood sampling was conducted at 5 min intervals from the circuit to confirm Timentin levels and 15 min intervals for clinical pathology measures. Following the PILP procedure, the catheters were removed and the animals recovered. Systemic blood samples were also taken 24 hours post procedure. At five (n=5) or ten (n=5) days post procedure, animals were euthanized and the following samples collected for histological analysis: proximal and distal femoral artery, vein, nerve and skeletal muscle.

In addition, isolated endothelial cells were exposed to Timentin (620, 1240, 2480, 4960 µg/ml) for 24 hours to determine any effect of the antibiotic.

Results

Figure 9:
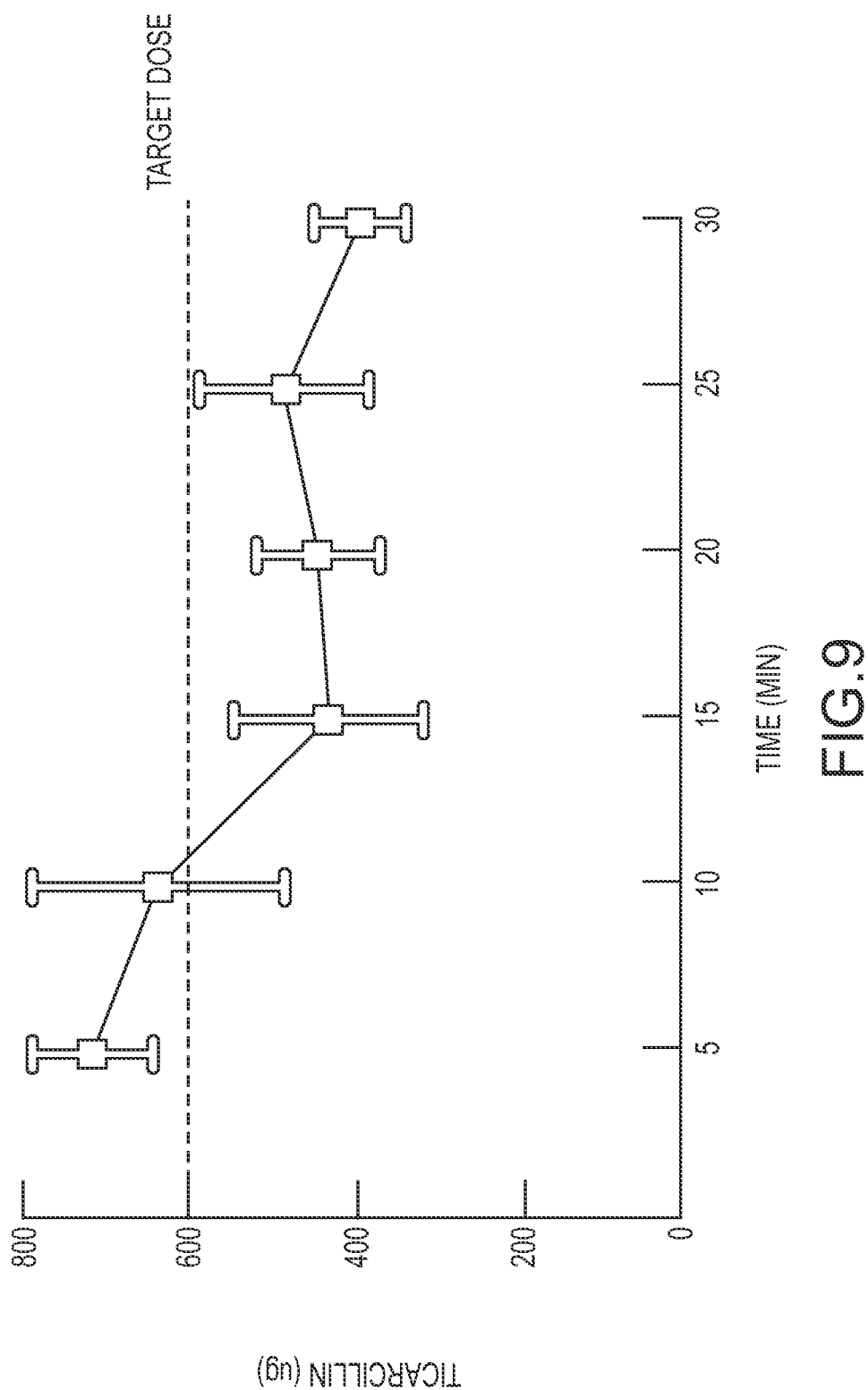
FIG. 9 is a chart depicting medicament levels during a perfusion procedure.

A Liquid Chromatography Mass Spectrometry (LC-MS) assay was conducted by an independent laboratory to determine the levels of the component of Timentin, Ticarcillin, levels during the PILP procedure. During the recirculation procedure, Ticarcillin levels were maintained at levels equivalent to the systemic dose delivered to patients (600 µg/ml). FIG. 9 depicts Ticarcillin levels achieved during the PILP procedure over 30 min of recirculation, values are mean±sem.

CONCLUSIONS

There were no significant differences in clinical pathology data in response to isolated delivery of Timentin during recirculation or at the 5 and 10 day time points. Histological analysis by an independent pathologist indicated that there was no significant histological changes in the tissues collected and no evidence of endothelial necrosis in multiple arteries or veins examined, nor was there evidence of any significant pathological change in the skeletal muscle or the peripheral nerves examined. Clinical Pathology Data is depicted in FIGS. 10-10A. Additionally, endothelial cells exposed to Timentin (620, 1240, 2480, 4960 µg/ml) for 24 hours did not show any cellular damage. Delivery of the antibiotic Timentin using the PILP system to the hind limb of normal sheep did not result in a pathological response.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured all such modifications as fall within the spirit and scope of the technology. Accordingly, what is desired to be secured by Letters Patent is the technology as defined and differentiated herein, and all equivalents.

What is claimed is:

1. A method of delivering a medicament to a limb of a patient body, the method comprising:
   isolating a circulatory system of the limb from a circulatory system of the patient body, wherein the limb circulatory system comprises substantially all limb arteries and substantially all limb veins located between an isolation region and an end of the limb;
   inserting a perfusion catheter into a limb artery of the limb circulatory system in an antegrade position;
   inserting a collection catheter into a limb vein of the limb circulatory system in a retrograde position, wherein an expandable non-occlusive support structure is at least partially disposed in the collection catheter during insertion, and wherein the perfusion catheter and the collection catheter each comprise an occlusion member constructed so as to move along a respective catheter;
   extending the expandable non-occlusive support structure from the collection catheter so as to expand the expandable non-occlusive support structure within the limb vein;
   circulating substantially all of a blood flow of the limb circulatory system by collecting the blood flow with the collection catheter and delivering the blood flow with the perfusion catheter; and
   perfusing a medicament to the limb circulatory system with the perfusion catheter.

2. The method of claim 1, wherein the isolating operation comprises applying a tourniquet to the limb.

3. The method of claim 1, wherein the isolating operation comprises expanding an occlusion device surrounding the perfusion catheter and expanding an occlusion device surrounding the collection catheter.

4. The method of claim 1, wherein the expandable non-occlusive support structure comprises a plurality of expandable members.

5. The method of claim 1, wherein the expandable non-occlusive support structure comprises a plurality of expandable members, and wherein at least one expandable member is secured to a distal end of the collection catheter.

6. The method of claim 1, wherein the circulating step is performed with a pump located external to the patient body.

7. The method of claim 6, wherein the pump circulates the blood flow at a rate of about 200 ml per minute to about 300 ml per minute.

8. The method of claim 1, further comprising at least one of oxygenating the blood flow and heating the blood flow.

9. The method of claim 1, wherein the medicament comprises at least one of antibiotics, anti-thrombin agents, anti-platelet agents, anti-spasm agents, and thrombolytic agents.

10. The method of claim 1, wherein the medicament comprises Timentin.

\* \* \* \* \*